United States Patent [19]

Lippmann

[11] 4,405,625

[45] Sep. 20, 1983

[54] METHOD OF TREATING HYPERGLYCEMIA WITH 1,3-DIOXO-1H-BENZ[DE]ISOQUINOLINE-2(3H)-ACETIC ACID

[75] Inventor: Wilbur Lippmann, Montreal, Canada

[73] Assignee: Ayerst, McKenna and Harrison Limited, Montreal, Canada

[21] Appl. No.: 45,376

[22] Filed: Jun. 4, 1979

Related U.S. Application Data

[63] Continuation of Ser. No. 862,801, Dec. 21, 1977, abandoned, which is a continuation-in-part of Ser. No. 818,379, Jul. 25, 1977, Pat. No. 4,118,495.

[51] Int. Cl.³ ............................................. A61K 31/47
[52] U.S. Cl. .................................................... 424/258
[58] Field of Search .......................................... 424/258

[56] References Cited

U.S. PATENT DOCUMENTS 3,821,383  6/1974  Sestans ................................. 424/258

OTHER PUBLICATIONS

*Science*, Dec. 14, 1973, vol. 181, pp. 1146–1148, Dvornik et al.

*Primary Examiner*—Frederick E. Waddell
*Attorney, Agent, or Firm*—Adley F. Mandel

[57] ABSTRACT

A method is disclosed for lowering blood glucose levels in a diabetic mammal by administering an effective amount of 1,3-dioxo-1H-benz[de]isoquinoline-2(3H)-acetic acid.

11 Claims, No Drawings

METHOD OF TREATING HYPERGLYCEMIA WITH 1,3-DIOXO-1H-BENZ[de]ISOQUINOLINE-2(3H)-ACETIC ACID

This is a continuation of application Ser. No. 862,801, filed Dec. 21, 1977, now abandoned, which is a continuation-in-part of application Ser. No. 818,379 filed July 25, 1977, now U.S. Pat. No. 4,118,495, issued Oct. 3, 1978.

BACKGROUND OF THE INVENTION (a) Field of Invention

This invention relates to a method for lowering blood glucose levels in a mammal suffering from diabetes mellitus. More particularly, it pertains to a method for diabetic control of a subject by administering 1,3-dioxo-1H-benz[de]isoquinoline-2(3H)-acetic acid.

(b) Prior Art

For many years diabetes mellitus has been treated with drugs by two established methods, one by administering insulin and the other by administering oral hypoglycemic agents. These methods have benefited hundreds of thousands of diabetics by improving their well-being and prolonging their lives. However, both of these methods have been used with certain reservations. Treatment with insulin requires ordinarily that the diabetic self adminster injections of insulin on a daily basis. This practice introduces the hazards of improper measurements and non-septic injection techniques aside from the grave disadvantage of repeated injections. In addition, continued daily injections of insulin can lead to an immune response to insulin. The use of the presently available oral diabetic agents also has been associated with reservations. Although these agents, for example, tolbutamide, tolazamide, acetohexamide, chlorpropamide and phenformin, can be used effectively for treating diabetes mellitus in most cases, the continued use of these agents has been associated with a significant incidence of serious side effects such as to warrant cautious use of these agents; for example, see S. A. Hagg in "Drug Therapy Reviews," Vol. 1, R. R. Miller and D. J. Greenblatt, Ed., Masson Publishing U.S.A., Inc., New York, Paris, Barcelona and Milan, 1977, p. 277. In addition, the oral hypoglycemic agents can be used only for the treatment of maturity-onset diabetes wherein the diabetic has some insulin secreting pancreatic beta cells.

Accordingly, there is a need for a therapeutic method for treating diabetes mellitus which is safe, reliable and which can be administered conveniently.

Surprisingly, I have now found that 1,3-dioxo-1H-benz[de]isoquinoline-2(3H)-acetic acid, or a therapeutically acceptable salt thereof, is an effective hypoglycemic agent when administered to diabetic humans and animals. This finding, coupled with the fact that this agent is a relatively safe drug, renders the method of this invention particularly useful and advantageous.

The active agent of this invention, 1,3-dioxo-1H-benz[de]isoquinoline-2(3H)-acetic acid, or a therapeutically acceptable salt thereof, is disclosed in U.S. Pat. No. 3,821,385, issued June 28, 1974. This active agent, hereinafter sometimes designated as "alrestatin," previously has been reported to be an inhibitor of the enzyme aldose reductase, and to be useful in preventing or relieving diabetic complications such as cataracts, neuropathy, nephropathy and retinopathy (see U.S. Pat. No. 3,821,383, cited above).

SUMMARY OF THE INVENTION

According to this invention a method is provided for lowering blood glucose levels in a diabetic mammal which comprises administering to said mammal a hypoglycemically effective amount of 1,3-dioxo-1H-benz[de]isoquinoline-2(3H)-acetic acid, or a therapeutically acceptable salt thereof.

A preferred form of administration is oral.

DETAILS OF THE INVENTION

According to the present method, alrestatin, either in its free acid form or in the therapeutically acceptable salt form, is employed as the active agent. Examples of suitable salt forms are described in U.S. Pat. No. 3,821,383 and include the sodium, potassium, magnesium, triethylamine and benzylamine salt forms. A preferred salt form is the sodium salt, i.e. alrestatin sodium.

Alrestatin, or a therapeutically acceptable addition salt thereof, is administered either orally or parenterally to a subject suffering from hyperglycemia for the purpose of managing diabetes mellitus. For many reasons oral administration is preferred.

While alrestatin or a therapeutically acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 3,821,383, cited above, herein incorporated by reference.

When utilizing alrestatin or one of its above-noted salts as agents for reducing or preventing hyperglycemia, the total dose of active agent can range from 1.0 to 1000 mg per kilogram of body weight per day with a preferred dosage range of from 50 to 200 mg per kilogram of body weight per day. Generally, a parenteral dose or an oral dose is administered two to four times per day. Such doses are considered to be effective amounts when, following their administration, the levels of glucose, with reference to blood, serum or plasma, are significantly reduced.

An experiment which demonstrates the effectiveness of alrestatin sodium in decreasing plasma glucose levels and increasing plasma insulin levels, involves measuring the changes in these levels caused by the administration of alrestatin sodium to anaesthetized fasted non-diabetic male intact rats subjected to an intravenous glucose tolerance test. A description of this experiment is as follows.

Male Sprague Dawley rats (200–250 g, Canadian Breeding Laboratories, St. Constant, Quebec, Canada) were used in the experiment. There were 11 animals in the group. The animals were kept in a room with constant light-dark cycle and temperature. They were allowed food (Purina Lab Chow TM) and water ad libitum for at least three days before being utilized. The animals were then fasted for 24 hours and anaesthetized with nembutal (50 mg/kg, intraperitoneally; Abbott Laboratories, Montreal, Quebec, Canada.) The jugular veins were exposed and a fasting blood sample was drawn by the transmusculature puncture method, Y. Kato, J. Dupré and J. C. Beck, Endocrinology,, 93, 135 (1973), employing a sodium heparin (The Upjohn Company, Don Mills, Ontario, Canada) washed syringe. Alrestatin sodium at a dose of 0.75 mmol/kg was administered as a bolus in the jugular vein followed immediately by a bolus of D-glucose (300 mg/kg; British Drug House, Montreal, Quebec, Canada). Control animals received an injection of sodium chloride (0.75 mmol/kg) instead of the alrestatin sodium. Blood samples were drawn at 5, 10 and 15 minutes after injection of the glucose. The wounds then were closed with autoclips (Clay Adams Co., Parsippany, N. J., U.S.A.) and the animals were allowed food and water for another three day period before the experiment was repeated, i.e., on day 4. At this time animals, which had previously been injected with alrestatin sodium, received the sodium chloride, and animals which had received sodium chloride were injected with alrestatin sodium. Blood samples were drawn by veinpuncture at the times indicated above. In a second in vivo study another group of animals was treated as above except no glucose was administered, six animals received the alrestatin sodium and six the sodium chloride.

Plasma insulin was measured by radioimmunoassay using a charcoal separation method, V. Herbert et al, J. Clin. Endocrinol., 25, 1375 (1965). $I^{125}$-Insulin was purchased from New England Nuclear, Lachine, Quebec, Canada, and purified before use on a DEAE-cellulose column as described by J. D. Curtis, M. Sc. Thesis, McGill University, Montreal, Quebec, Canada, 1968. Rat insulin (Novo A/S, Copenhagen, Denmark) was used as standard. Antiserum to rat insulin, kindly provided by Dr. J. Dupré (University of Western Ontario, London, Ontario), was used as the antibody. Plasma glucose was measured by a glucose oxidase method employing a Beckman Glucose Analyser, see Beckman Company Manual, Palo Alto, Calif., U.S.A.

The results, noted below, are expressed as mean± S.E.M. The statistical significance of changes in the concentration of plasma glucose (mg/100 ml) and insulin ($\mu$U/ml), in response to alrestatin or the vehicle, from basal fasting values was determined on the differences between group means by the Student's ±-test. Furthermore, p values less than 0.05 were considered to be significant.

The basal fasting glucose and insulin levels for the animals on days 1 and 4 of the study were similar thus indicating that surgical intervention and bleedings on day 1 did not alter hormone or glucose levels which have been shown to be changed during acute stress.

The mean incremental changes of plasma glucose after the bolus of intravenous glucose were similar for both treatments at five minutes (vehicle: 96±4.7 mg %; alrestatin: 83.3±5.4 mg %, NS). The mean increments of glucose were significantly lower (p<0.05) in the alrestatin sodium treated animals both at ten minutes (vehicle: 82.8±7.5 mg %; alrestatin: 58.8±8.5 mg %) and at 15 minutes (vehicle: 78.4±10.7 mg %; alrestatin: 45.4±9.6 mg %).

The mean incremental changes of plasma insulin were observed at five minutes after glucose injection in both treatments. At this time and at ten minutes, plasma insulin levels were significantly greater in the alrestatin sodium treated groups at five minutes (vehicle 32.9±5.2 $\mu$U/ml; alrestatin: 76.9±16.7 $\mu$U/ml; p<0.02). The insulin levels were greater at 15 minutes in the alrestatin treated group although the difference was not significant.

Note that in a control group of animals which did not receive the bolus of intravenous glucose, the acute administration of alrestatin did not significantly alter either the change in the basal fasting plasma insulin levels or in the plasma glucose levels from those levels observed for the animals treated with the vehicle.

The above findings show that alrestatin acts to augment glucose-induced insulin secretion in the intact rat. The ability of alrestatin to cause an augmentation of insulin release is not specific for glucose since alrestatin also can increase arginine-induced insulin release (and decrease arginine-induced glucagon release) in the intact rat. These effects on insulin and glucagon are desirable actions for a hypoglycemic agent. The effects are demonstrated by the following experiment.

Male Sprague-Dawley rats (225-275 g; Canadian Breeding Laboratories, St. Constant, Quebec, Canada) were allowed access to food (Purina Lab Chow ™) and water ad libitum for a minimum of five days before experiments were conducted. After light deithyl ether anaesthetization, the animals were injected with a bolus of saline or alrestatin (sodium salt form in 0.3 ml saline/100 g of body weight) in the external jugular vein followed immediately with a bolus of arginine-HCl (British Drug House) at a dose of 100 mg/100 g of body weight, cf. M. Brown et al., Endocrinology, 98, 336(1976). Vehicle control animals received a second injection of saline. Five minutes later trunk blood was collected by decapitation into chilled tubes containing sodium heparin (Upjohn) and aprotinin(Trasylol ™, Boehringer-Ingelheim Dorval, Quebec, Canada) (20 U and 1000 KIU per ml whole blood, respectively). Plasma was collected after centrifugation, stored at $-20°$ C. and assayed for immunoreactive glucagon and insulin levels within 2 weeks.

Plasma insulin was assayed with antiserum to rat insulin $I^{125}$-Insulin tracer was purchaced from New England Nuclear, Lachine, Quebec, Canada, and purified before use on a DEAE-cellulose column (J. D. Curtis, M.Sc. Thesis, McGill University, Montreal, Quebec, Canada, 1968). Rat insulin purchased from Novo A/S, Copenhagen, Denmark, was used as unlabelled standard. Plasma glucagon was assayed by the method of G. R. Faloona and R. H. Unger in "Methods of Hormone Radioimmunoassay," J. Behmann, Ed., Academic Press, New York, N.Y., 1974, with two modifications, i.e., the tubes were not precoated with gelatin, and normal lamb serum was omitted from the glycine buffer; these modifications did not alter the binding of glucagon or the non-specific binding. Glucagon antiserum (Antiserum 30K, purchased from Dr. R. H. Unger, Houston, Tex., U.S.A.) was employed in the assay. $I^{125}$-Glucagon purchased from Nuclear Medical Laboratories, Dallas, Texas, was purified according to the method of K. H. Jorgensen and O. D. Larsen, Horm. Metab. Res., 4, 223 (1972). Procine glucagon, which has been demonstrated to be identical to rat glucagon, F. Sundby and J. Markussen, Horm. Metab. Res., 3, 184 (1971), was purchased from Novo A/S and was used as the standard. Antibody bound hormone was separated from free hormone by conventional charcoal-dextran methods.

Regarding glucagon response, arginine (100 mg/100 g of body weight) stimulated glucagon release to a mean of about 100 pg/ml above the plasma hormone concentration in the vehicle treated animals (arginine: 284.8±13.7 pg/ml vs vehicles: 180.6±5.8 pg/ml). Alrestatin sodium administered immediately before arginine decreased the glucagon concentrations in the dose range examined, i.e., 35-200 mg/kg; alrestatin sodium at 200 mg/kg completely prevented the increase caused by arginine.

Regarding insulin response, arginine administration increased the plasma insulin concentration by about 100

μU/ml. Alrestatin sodium increased the insulin release observed with arginine in the dose range examined, i.e., 35–200 mg/kg; the insulin release was increased by about 2.5 fold by alrestatin sodium at 200 mg/kg.

The preceding findings that the active agent, alrestatin is capable of stimulating insulin release while inhibiting glucagon release in noteworthy indeed, since diabetes mellitus is characterized by both insulin deficiency and glucagon excess, R. Unger, Diabetes, 25, 136 (1976). More particularly, diabetes mellitus is a bihormonal disorder characterized not only by a relative or absolute insufficieny of insulin but also by a relative or absolute excess of glucagon, W. A. Müller, G. R. Faloona and R. H. Unger, Am. J. Med., 54, 52 (1973). The established methods for treating the bihormonal disorder of diabetes are aimed only a correcting the lack of insulin. On the other hand, the method of this invention beneficially affects this bihormonal balance whereby diabetic control, e.g. lower mean diurnal glucose levels, lower glucose peaks after meals and high glucose nadirs before meals, is better achieved in both the juvenile and maturity-onset diabetic.

Indeed, because the method of this invention tends to normalize the relationship between insulin and glucagon, application of the method of this invention for treating diabetics dependent on insulin supplements permits a reduction in the daily requirement of exogenous insulin, as determined by the physician. In other words, the administration of alrestatin plus a suboptimal dose of insulin or oral hypoglycemic agent, provides for improved diabetic control of such patients, with a saving in insulin.

Clinical tests in diabetic patients further demonstrate the efficacy of the method of this invention for lowering blood glucose levels. For example, intravenous administration of alrestatin sodium (50 mg/kg/day) for five days was effective in lowering blood sugar levels of diabetic patients, as illustrated in the following table.

| DAY | PATIENT A BLOOD GLUCOSE (mg %) | | PATIENT B BLOOD GLUCOSE (mg %) | | PATIENT C BLOOD GLUCOSE (mg %) | |
|---|---|---|---|---|---|---|
| | Fasting | 2hr Postprandial | Fasting | 2hr Postprandial | Fasting | 2hr Postprandial |
| Pretreatment | 162 | 276 | 90 | 119 | 95 | 190 |
| 1 | 132 | 185 | 92 | 72 | 133 | 128 |
| 2 | 130 | 215 | 89 | 86 | 111 | 145 |
| 3 | 97 | 155 | 86 | 94 | 104 | 141 |
| 4 | 90 | 117 | 50 | 60 | 50 | 90 |
| 5 | 132 | 230 | 50 | 43 | 77 | 106 |
| Follow-up | 111 | 207 | 81 | 87 | 119 | 149 |

All patients were on a controlled diet. Patient A also was receiving the oral antidiabetic agent, glyburide (Daonil TM) and patient C also was receiving the diuretic chlorthalidone (Hygroton TM).

Finally, the $LD_{50}$ of alrestatin in rats according to the route of administration is greater than 2,500 mg/kg (perorally), 1220±45 mg/kg (intravenously), and 1380±mg/kg (intraperitoneally). Therefore, a good therapeutic index of safety is present.

I claim:

1. A method for lowering blood glucose levels in a diabetic mammal suffering from hyperglycemia which comprises administering to said mammal a hypoglycemically effective amount of 1,3-dioxo-1H-benz[de]isoquinoline-2(3H)-acetic acid or a therapeutically acceptable salt thereof.

2. The method of claim 1 in which the effective amount of 1,3-dioxo-1H-benz[de]isoquinoline-2(3H)-acetic acid is within the range of 1.0 to 1000 mg per kilogram of body weight per day.

3. The method of claim 1 in which the effective amount of 1,3-dioxo-1H-benz[de]isoquinoline-2(3H)-acetic acid is within the range of 50 to 200 mg per kilogram of body weight per day.

4. The method of claim 1 in which the therapeutically acceptable salt is the sodium salt.

5. The method of claim 1 in which the administration is oral.

6. A method for stimulating insulin release while inhibiting glucagon release in a diabetic mammal suffering from an insulin deficiency and hyperglucagonemia which comprises administering to said mammal a hypoglycemically effective amount of 1,3-dioxo-1H-benz[de]-isoquinoline-2(3H)-acetic acid or a therapeutically acceptable salt thereof.

7. The method of claim 6 in which the effective amount of 1,3-dioxo-1H-benz[de]isoquinoline-2(3H)-acetic acid is within the range of 50 to 200 mg per kilogram of body weight per day.

8. The method of claim 6 in which the effective amount of 1,3-dioxo-1H-benz[de]isoquinoline-2(3H)-acetic acid is within the range of 50 to 200 mg per kilogram of body weight per day.

9. A method of stimulating insulin release in a diabetic mammal suffering from an insulin deficiency which comprises administering to said mammal a hypoglycemically effective amount of 1,3-dioxo-1H-benz[de]isoquinoline-2(3H)-acetic acid or a therapeutically acceptable salt thereof.

10. The method of claim 9 in which the effective amount of 1,3-dioxo-1H-benz[de]isoquinoline-2(3H)-acetic acid is within the range of 1.0 to 1000 mg per kilogram of body weight per day.

11. The method of claim 9 in which the effective amount of 1,3-dioxo-1H-benz[de]isoquinoline-2(3H)-acetic acid is within the range of 50 to 200 mg per kilogram of body weight per day.

* * * * *